US009964750B2

(12) United States Patent
Rozsa et al.

(10) Patent No.: US 9,964,750 B2
(45) Date of Patent: May 8, 2018

(54) OPTICAL MICROSCOPE SYSTEM FOR SIMULTANEOUS OBSERVATION OF SPATIALLY DISTINCT REGIONS OF INTEREST

(71) Applicant: Femtonics Kft., Budapest (HU)

(72) Inventors: Balazs Jozsef Rozsa, Budapest (HU); Gergely Katona, Budapest (HU); Pal Andor Maak, Budapest (HU)

(73) Assignee: Femtonics Kft., Budapest (HU)

( * ) Notice: Subject to any disclaimer, the term of this patent is extended or adjusted under 35 U.S.C. 154(b) by 0 days. days.

(21) Appl. No.: 15/039,601

(22) PCT Filed: Nov. 28, 2013

(86) PCT No.: PCT/HU2013/000114
§ 371 (c)(1),
(2) Date: May 26, 2016

(87) PCT Pub. No.: WO2015/079268
PCT Pub. Date: Jun. 4, 2015

(65) Prior Publication Data
US 2017/0212342 A1 Jul. 27, 2017

(51) Int. Cl.
*G02B 21/18* (2006.01)
*G02B 21/00* (2006.01)
*A61B 3/13* (2006.01)
*A61B 3/14* (2006.01)
*A61B 5/00* (2006.01)

(52) U.S. Cl.
CPC .............. *G02B 21/18* (2013.01); *A61B 3/13* (2013.01); *A61B 3/14* (2013.01); *A61B 5/0071* (2013.01); *A61B 5/40* (2013.01); *G02B 21/0032* (2013.01); *G02B 21/0052* (2013.01); *G02B 21/0076* (2013.01)

(58) Field of Classification Search
CPC ...... G02B 21/18; G02B 21/0032; A61B 3/13; A61B 3/14; A61B 5/0071; A61B 5/40
USPC ................................. 359/372, 368
See application file for complete search history.

(56) References Cited

U.S. PATENT DOCUMENTS

| 4,417,789 A | * | 11/1983 | Kano | G02B 21/18 359/373 |
| 5,812,269 A | * | 9/1998 | Svetkoff | G01B 11/24 250/559.23 |
| 6,061,086 A | * | 5/2000 | Reimer | G01N 21/8851 348/125 |
| 7,015,444 B2 | * | 3/2006 | Kawano | G02B 21/004 250/201.3 |

(Continued)

Primary Examiner — William R Alexander
(74) Attorney, Agent, or Firm — Olson & Cepuritis, Ltd.

(57) ABSTRACT

The invention relates to an optical microscope system (10) for the simultaneous measurement of at least two spatially distinct regions of interest, characterized by comprising at least two distinct optical measuring heads (12a, 12b, 12c) that can be simultaneously focused on spatially distinct arbitrary regions of interest, each optical measuring head is optically connectable with at least one scan head (14), the optical microscope system further comprising a control system (32) connected to the at least one scan head and the optical measuring head, the control system being configured to provide for synchronized control of the operation of the at least one scan head and the at least two optical measuring head.

15 Claims, 2 Drawing Sheets

(56) References Cited

U.S. PATENT DOCUMENTS

| | | | |
|---|---|---|---|
| 2005/0211872 A1* | 9/2005 | Kawano | G02B 21/004 250/201.3 |
| 2009/0153824 A1* | 6/2009 | Balan | G03B 27/42 355/67 |
| 2009/0180177 A1* | 7/2009 | Gilbert | G01N 21/95607 359/373 |
| 2010/0088787 A1* | 4/2010 | Shigekawa | B82Y 35/00 850/6 |
| 2013/0162994 A1* | 6/2013 | Xie | G01N 21/171 356/342 |

* cited by examiner

OPTICAL MICROSCOPE SYSTEM FOR SIMULTANEOUS OBSERVATION OF SPATIALLY DISTINCT REGIONS OF INTEREST

CROSS-REFERENCE TO RELATED APPLICATION

This application is a U.S. National Phase of PCT/HU2013/000114, filed Nov. 28, 2013, which is incorporated herein by reference.

The present invention relates to an optical microscope system that allows for the simultaneous measurement of neural activity in at least two spatially distinct regions of interest in the nervous system of a vertebrate.

Various microscopy technologies have great importance in analysing biological specimens e.g. imaging structures and assessing functional activity based on fluorescence emission.

One of the commonly applied technologies involves the use of 3D laser scanning microscopes that can be either confocal microscopes or multi-photon microscopes. In the confocal microscope technology a pinhole is arranged before the detector to filter out light emitted or reflected from any other plane than the focus plane of the microscope objective. Thereby it is possible to image planes lying in different depths within a sample (e.g. a biological specimen).

Multi-photon laser scanning microscopes use a laser light of lower photon energy of which two or more photons are needed to excite a fluorophore in a quantum event, resulting in the emission of a fluorescence photon, which is then detected by a detector. The probability of a near simultaneous absorption of two or more photons is extremely low requiring a high flux of excitation photons, thus multi-photon excitation practically only occurs in the focal spot of the laser beam, i.e. a small ellipsoidal volume having typically a size of approximately 320 nm×320 nm×1000 nm. Generally a femtosecond pulsed laser is used to provide the required peak photon flux for the multi-photon excitation, while keeping the average laser beam intensity below the specimen's damage threshold.

When applying either of the above-mentioned technologies the 3D scanning of the exciting laser focal spot can be carried out by moving the sample stage e.g. via stepping motors, however this is complicated to implement when using submerge specimen chambers or when electrical recording is performed on the biological specimen with microelectrodes. Accordingly, in the case of analysing biological specimens it is often preferred to move the focal spot of the laser beam instead of moving the specimen. This can be achieved by deflecting the laser beam to scan different points of a focal plane (XY plane) and by displacing the objective along its optical axis (Z axis) e.g. via a piezo-positioner to change the depth of the focal plane. Several known technologies exist for deflecting the laser beam prior to entering the objective, e.g. via deflecting mirrors mounted on galvanometric scanners, or via acousto-optical deflectors.

A further technology is holographic microscopy, where different sample points are addressed using different diffraction patterns of different holograms, somewhat similar to scanning.

In case of all aforementioned technologies, the number of the sample points examined within one fast scanning sequence (corresponding to one image or one measurement entity performed with the biggest temporal resolution) is limited by the field of view of the optical imaging system of the microscope. Hence, if a larger region of interest or a plurality of spatially distinct regions of interest have to be measured, then such measurements must be conducted sequentially by scanning the one or more regions of interest, loosing the temporal resolution necessary to follow the desired functional processes. For example, despite the distributed nature of all brain computations, the prior art technology for high-throughput recordings at several distant brain regions capable to spatially resolve neurons or even neuronal compartments is entirely lacking. Moreover, stimulation-recording pairs also cannot be performed with proper temporal and spatial resolution at distant brain regions. The current state-of-the-art technology is high-resolution two-photon imaging or stimulation-recording within one brain region with a volume of approximately 700×700×2000 µm3.

The inventors have realised that for certain types of examinations it would be important to be able to perform measurements nearly simultaneously (with high temporal resolution) on distinct regions of interest that are spatially spaced apart from each other. For example, brain computations are distributed over large distances; hence it is difficult to study all neuronal circuits involved in any particular task. One example is the visual system, where the image that enters the eye is processed in the retina (located in the eye), the lateral *geniculate* nucleus (LGN) (located centrally in the brain), and the visual cortex (close to the surface of the brain). Understanding such distributed brain computations requires methods that can simultaneously report neuronal activity in functionally connected but distant regions. Despite the large distances (not able to be scanned within one scanning sequence) between connected brain regions, within each site the computation is performed by small neuronal microcircuits, or even the neuronal compartments of a single neuron, such as dendrites or axons. Therefore it is needed to record (measure) the activity at a sub-micron spatial resolution in a given region, but it is also needed to perform such recordings simultaneously in different regions, perhaps separated by millimeters or centimeters. Since parallel computations within each brain region are performed by different but physically overlapping microcircuits, a combination of recording and powerful genetic methods is needed to allow recording from identified circuits. Finally, there is a need not only to record, but also to stimulate identified neurons or circuits in a given brain region while recording the evoked activity in other regions to demonstrate a causal link between stimulation and distant neuronal activity.

On the one hand methods such as MRI and PET can simultaneously record distant and deep brain regions, but the resolution is far from resolving individual neurons. On the other hand optical microscopy (such as confocal microscopy, two-photon microscopy and holographic microscopy) provides the necessary temporal and spatial resolution, but is currently capable to scan only the above defined field of view limited volume, hence it is also unsuitable for carrying out the above measurements.

In "Simultaneous imaging of multiple focal planes using a two-photon scanning microscope" (Optics Letters, Vol. 32, No. 12, Jun. 15, 2007) Amir et al. propose to temporally demultiplex the signal coming from two or more focal volumes at different sample depths. The disadvantage of the proposed method is that a single objective is used whereby the location of the simultaneously imaged focal volumes are not arbitrary, which makes this technology unsuitable for carrying out e.g. the above described simultaneous measurements (stimulation and recording) on distinct brain regions that are separated by millimeters or even centimeters.

Hence, it is an object of the present invention to provide an optical microscope system for the simultaneous measurement of at least two spatially distinct, arbitrary regions of interest by being able to simultaneously focus on such regions of interest with the use of at least two optical measuring heads. In particular it is an object of the invention to provide such simultaneous focusing even in case that the regions of interest are spaced apart from each other by a distance in the millimeter or centimeter range.

The above objectives are achieved by an optical microscope system according to claim 1 and a method according to claim 16.

Further advantageous embodiments of the invention are defined in the attached dependent claims.

In the context of the present invention the term "measurement" is understand to include photo stimulation/activation, imaging, electrical and optical recording of stimulations and functional processes, and similar processes.

In the context of the present invention the term "region of interest" refers to a 2-dimensional area or a 3-dimensional volume, where it is desired to perform a measurement.

In the context of the present invention the term "optical measuring head" may refer to an objective, a lens system, a single lens (e.g. a GRIN lens), and any other data collecting devices, or any combination thereof.

In the context of the present invention the term "scan head" refers to one or more units that may comprise optical elements for deflecting an optical beam in the X, Y, Z directions (Z being the optical axis), dispersion compensators, beam stabilisers, beam expanders, and similar devices commonly used for directing an optical beam to a desired location.

The scan head is said to be "optically connectable" with an optical measuring head if an optical path can be created between the scan head and the optical measuring head such that an optical beam exiting the scan head enters the optical measuring head. This is also referred to as optical coupling.

Further details of the invention will be apparent from the accompanying figures and exemplary embodiments.

Figure 1:
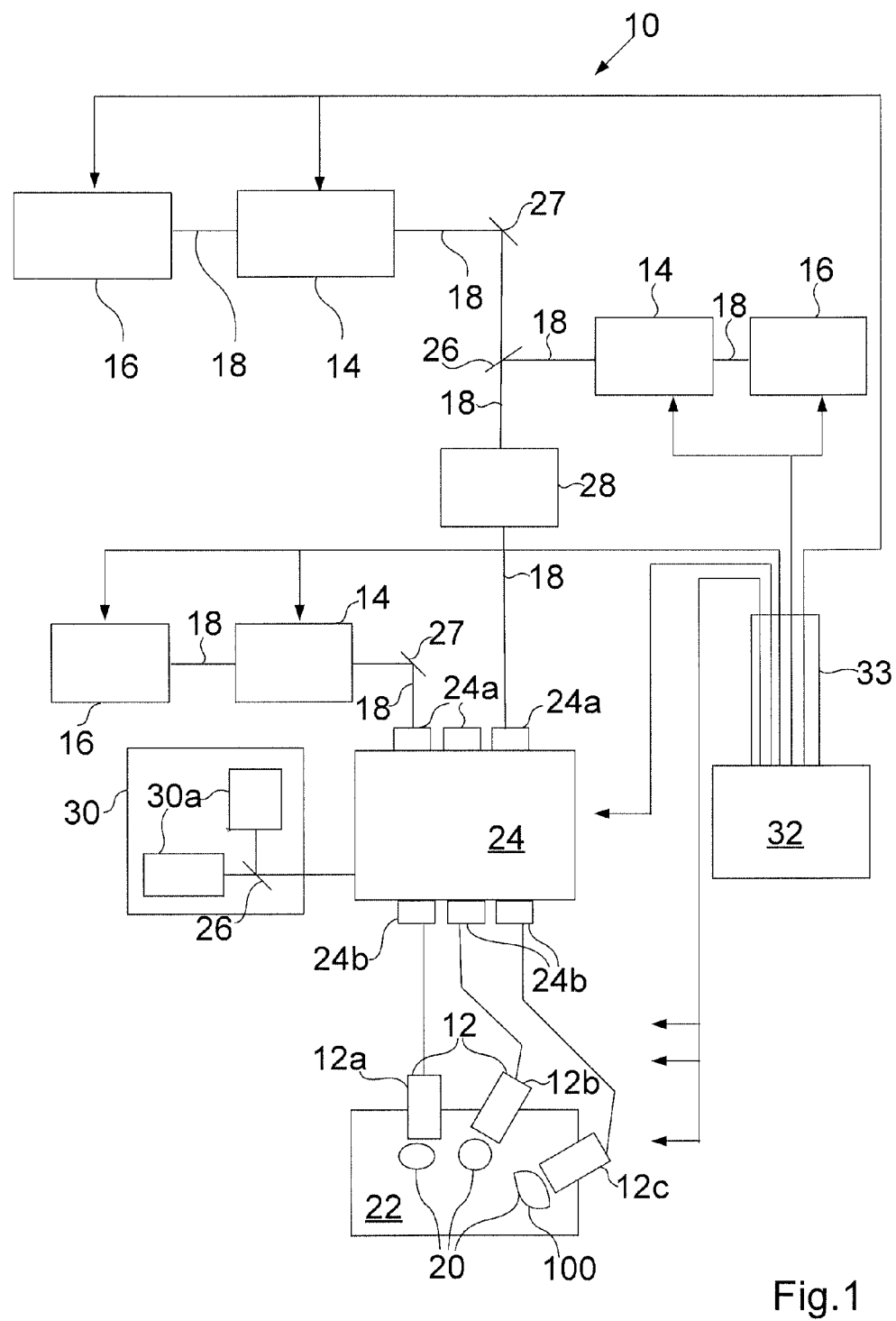
FIG. 1 is a schematic block diagram of an embodiment of an optical microscope system according to the invention.

FIG. 1 schematically illustrates a preferred embodiment of an optical microscope system 10 in accordance with the present invention. In this embodiment the microscope system 10 comprises three distinct optical measuring heads 12 (commonly referred to as measuring heads), three scan heads 14, three light sources 16 and may comprise various optical elements for guiding and keeping an optical beam 18 together (e.g. filters 26, mirrors 27, dispersion compensators 28, lenses 29, active optical systems (LCDs, acousto-optic or electro-optic devices etc.) to optically connect the components.

According to the present embodiment each light source 16 is a laser light source 16 comprising e.g. a titanium-sapphire (Ti:S) laser, that is preferably a tunable laser with the possibility of spectral tuning e.g. between 720 to 950 nm. It is also possible that some or all of the employed lasers have different wavelengths with wavelengths in the visible, NIR or UV ranges. Each laser source 16 is optically coupled to one of the scan heads 14 which serves to deflect the laser beam 18 provided by the laser source 16. Although in the present example each scan head 14 is depicted as being provided with a separate laser source 16, it is also conceivable that two or more scan heads 14 are wavelength tuned for the same wavelength in which case these scan heads 14 may share a common laser source 16 and the emitted laser beam 18 is split up, e.g. by known beam splitters, and guided to the scan heads 14 via suitable optical guiding elements (such as mirrors 27, lenses 28, etc.). It is also possible that the light sources 16 are external elements that are not part of the microscope system 10.

The laser source 16 (or any other type of light source 16, e.g. a lamp) may include beam quality enhancing components (or units) such as amplifiers, Faraday isolators, etc.

The scan heads 14 are optically interposed between the light sources 16 and the optical measuring heads 12 along the optical beam path to allow excitation beam scanning through the sample 22. The scan heads 14 may comprise any type of beam deflectors that are suitable for deflecting an optical beam such as to direct the focal spot of the beam exiting the corresponding optical measuring head 12 onto an arbitrary region of interest 20 of the sample 22. For example one of the scan heads 14 may comprise an acousto-optic deflector, while another one of the scan heads 14 may comprise deflecting mirrors mounted on galvanometric scanners, both of which are well known from the art. The scan heads 14 may comprise further optical components (or units) such as dispersion compensators, beam stabilisers, beam expanders, guiding mirrors, etc., furthermore, such optical components or units may be provided separately from the scan heads 14 within the microscope system 10.

Preferably at least one scan head 14 is suitable for performing 3-dimensional scanning and preferably at least one scan head 14 is capable of photoactivation.

It is also possible to use a single device in combination with more measuring heads 12, which device performs the functions of more than one scan heads 14. The simplest way to split the output of the scan head 14 to at least two parts is spectral filtering. The method needs a wide bandwidth (FWHM>20-25 nm) ultrashort pulsed laser. The spectrum can be split into two effective parts (both containing enough power for excitation), that can be directed separately to the measuring heads 12 using dichroic mirror with a selective spectral edge matched to the central wavelength of the pulse spectrum. The contrast can be enhanced using spectral bandpass filters as well.

The optical measuring head 12 can be any suitable optical element, or system of elements that are suitable for focusing the light beam 18 onto a region of interest 20 of a sample 22.

In the present example the first optical measuring head 12 is an objective 12a, which may be any type of suitable lens system for focusing the laser beam 18 provided by one of the laser sources 16 and deflected by one of the scan heads 14. For certain applications, such as the in vivo examination of brain activity of deeply lying brain parts, the objective 12a is preferably combined with any other type of lens providing optical matching, e.g. a micro-lens for aberration correction.

In the present embodiment the second optical measuring head 12 is a grin lens 12b or micro lens/GRIN lens sequence). Grin lenses 12b are special shaped glass units with spatially variable refractive index, which can be inserted into the examined tissue in order to reach deeper lying areas.

The simultaneous measuring (imaging and/or scanning and/or photo-stimulating, etc.) of three spatially non-overlapping regions of interest 20 are achieved according to the invention by three distinct (separate) optical measuring heads 12. Accordingly, each optical measuring head 12 should be placed under different angles and/or lateral positions, each being optimized for the position and orientation of the measured region of interest 20 (typically a volume of the sample 22), which arrangement imposes some constraints on the relative position and angle of the adjacent measuring heads 12, due to their size. The use of the elongated GRIN lens 12b (having a thickness of 1-2 mm) has the further advantage that the distance between the measured regions of interest 20 can be reduced, since it leaves more space to the adjacent measuring heads 12 than e.g. a microscope objective. This is particularly important in case of carrying out measurements over a small surface compared to the size of the commercial microscope objectives (e.g. when measuring the brain activity of rodents as mentioned earlier).

Figure 2:
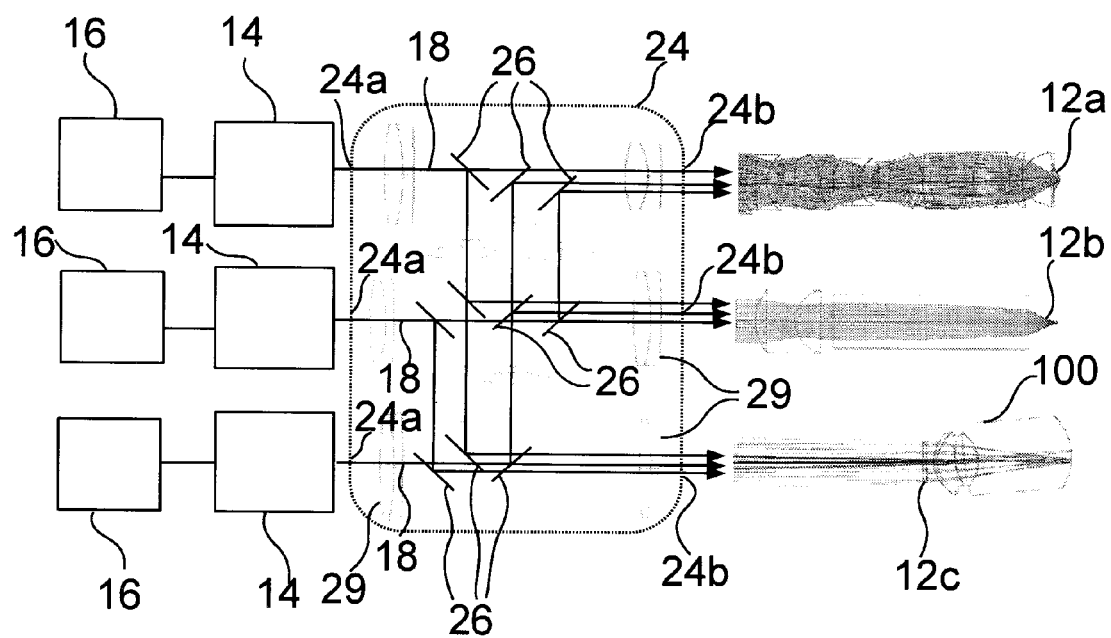
FIG. 2 is a schematic block diagram of an optical multiplexer that can be employed in the optical microscope system according to the invention.

The third optical measuring head 12 in the present embodiment is a lens 12c that is used as an optical adaptor for stimulation and imaging of an eye 100 (see FIG. 2).

By using distinct optical measuring heads 12 it is possible to simultaneously focus on spatially distinct (non-overlapping) arbitrary regions of interest 20 that are spaced from each other by a distance which is typically greater than 1 cm, but at least greater than 1 mm. This would not be possible using the simultaneous imaging of multiple focal planes, as suggested by Amir et al. and described above, where a single objective was used. The optical measuring heads 12 of the present invention are distinct in the sense that these have distinct optical axes, which do not coincide with each other.

For the purpose of the above described examination the technical solution for the stimulation and imaging of the retina is somewhat different from the task of brain imaging, since the eye 100 itself has considerable refractive optical power. Instead of using an objective, an adaptive lens 12c can be designed, which matches the eye 100 to at least one of the scan heads 14 and allows the deflected laser beam 18 to be focused onto the retina at the highest optical resolution found in the eye 100 (2-3 µm spot size). Such lenses 12c are available for the human eye in regular clinical examination setups, such as LENSTAR™, and can be designed with the same technology for any specific animal to be examined. The adaptive optical devices incorporated into the optical path help to optimize the focusing through the eye 100, and to obtain satisfactory performance both in stimulation and in imaging.

The size of each region of interest 20 where the measurement is to be performed may correspond to the size of a focal spot, i.e. a small volume into which the light beam 18 is focused when passing through the optical measuring head 12 (and possibly other optical guiding elements arranged upstream of the measuring head 12), or it may be a larger area or volume that is scanned by deflecting the beam with the optically coupled scan head 14 and by adjusting the focal depth of the optical measuring head 12.

The scan heads 14 are preferably each optically connectable with at least one optical measuring head 12, but preferably each scan head 14 is optically connectable with each measuring head 12 (i.e. the objective 12a, the GRIN lens 12b and the adaptive lens 12c in the illustrated case). In the context of the present invention optical connection (or optical coupling) between a given scan head 14 and a given optical measuring head 12 refers to the fact that a potential optical beam path is available along which the light beam 18 (including the possibility of a light pulse) would travel from the given scan head 14 to the given optical measuring head 12. In this sense the optical connection may be created permanently by permanently arranging optical guiding elements (e.g. mirrors 27, beam splitters, selective filters 26, optical fibres etc.), to create the desired optical beam path. However, in a preferred embodiment the optical connection is not permanent, but instead variable, meaning that the optical guiding elements can be rearranged in order to create different beam paths connecting different scan heads 14 with different measuring heads 12. The term "optically connectable" is understood to include both the possibility of permanent connection and variable connection.

According to a preferred embodiment the scan heads 14 are optically connectable with the measuring heads 12 via an optical multiplexer 24, such that optical guiding elements are arranged variably within the optical multiplexer 24 for creating different beam paths in order to connect different scan heads 14 with different measuring heads 12. The multiplexer 24 has input ports 24a, where the light beams 18 enter the multiplexer 24 and output ports 24b, where the light beams 18 exit. The multiplexer 24 may allow variable optical connection between any number of scan heads 14 and measuring heads 12, although it is not necessary that all the scan heads 14 and all the measuring heads 12 be connectable via the multiplexer 24, e.g. certain may be permanently optically connected outside the multiplexer 24. However, in the preferred embodiment depicted in FIG. 1, all measuring heads 12 and all scan heads 14 of a microscope are optically coupled to the multiplexer 24 such that each measuring head 12 is optically connected with one of the output ports 24b (i.e. an optical beam path is provided between the two) and each scan head 14 is optically connected with one of the input ports 24a (i.e. an optical beam path is provided between the two). Preferably each measuring head 12 is connected to a different output port 24b, while two or more scan heads 14 may be connected to the same input port 24a (see FIG. 1), if the scan heads 14 are tuned for different wavelengths (and the light sources 16 coupled therewith provide optical beams 18 of corresponding wavelength). In this case a wavelength selective filter 26 may be interposed in the optical beam paths (superposed e.g. to one or more mirrors 27), which reflects the beam 18 coming from one of the scan heads 14 (the first scan head 14) and is transparent to the other beam 18 coming from the other scan head 14 (the second scan head 14) whereby the two beams 18 are united into a single beam 18 on one side of the selective filter 26. Alternatively, the light sources 16 may provide optical beams 18 of different polarisation in which case polarisation selective filters may be used to unify the two beams 18. Preferably an angular dispersion compensator 28 is arranged along the unified optical beam path in order to compensate for any angular dispersion caused by the filter 26. In the embodiment depicted in FIG. 1 the optical beam 18 exiting the third scan head 14 is directed to a different input port 24a than the common input port 24a to which the first two scan heads 14 are connected optically.

It is also possible to optically connect each scan head 14 with a different input port 24a as depicted in FIG. 2.

A possible arrangement of the optical guiding elements is schematically illustrated in FIG. 2. By way of selective filters 26, e.g. wavelength selective or polarisation selective filters 26 any beam 18 entering any input port 24a may be guided to any output port 24b, whereby any laser source 16 and subsequent scan head 14 can be optically coupled with any one of the optical measuring heads 12. The different selective filters 26 may be grouped together and mounted on wheels and translational stages, with multiple filter holders or on sliding trays in order to vary the filter 26 inserted into the beam path, which determines which laser beam 18 is allowed to pass in the direction of a given output port 24b and which beam 18 is reflected so as to create a different beam path leading to a different output port 24b. The beam path separation is based on an optical property of the beams 18 (e.g. wavelength or polarisation). The consecutive arrangement of selective filters 26 and the technique of creating optical beam paths therewith are well known in the art, and may be realised by a multitude of configurations as will be apparent to the person skilled in the art.

The optical multiplexer 24 may comprise further conventional optical guiding elements for guiding and keeping the beam 18 collimated or imaging with proper magnification, e.g. mirrors 27 and lenses 29 as well as alternatively, optical fibres.

The optical multiplexer 24 has a further output port 24b that is connected to a detector unit 30 comprising one or more detectors 31 for detecting and providing measurement data. Any suitable detector 31 can be used, e.g. a photo multiplier, to detect emitted photons in the measured region of interest 20. Also, more than one detectors 31 provided with appropriate wavelength filters can be arranged in a known way if emitted photons of different wavelengths are to be detected separately.

The optical microscope system 10 according to the invention further comprises a control system 32 for the synchronised control of the operation of the microscope system 10. In particular at least the scan heads 14 and the optical measuring heads 12 are operable connected with the control system 32 in order to receive control signals from the control system 32. Synchronisation is a crucial aspect of performing simultaneous measurements (imaging, recording, stimulation, etc.), hence all the measuring units formed by the individual scan heads 14 and measuring heads 12 optically coupled therewith have to be controlled by a common control system 32 providing synchronised control signals for each measuring unit. Preferably the control system 32 allows for controlling measurements and photo stimulation in two, three or more spatially distinct locations (regions of interest 20) and for simultaneously collecting 3D measurement data.

Suitable control system 32 may be computer, microcontroller, dedicated control electronics or the like that may comprise (or be connected to) various input and output user interfaces e.g. for inputting commands and outputting measurement data and various calculation units for processing measurement data.

The control system 32 may further serve to control the operation of other components of the microscope system 10 as well, such as the light sources 16 (e.g. lasers) or stepping motors bringing the selective filters 26 mounted on holder wheels or positioning stages into the desired position within the optical multiplexer 24. However, such components may be controlled by a separate control device or even manually (e.g. the desired beam paths can be created within the multiplexer 24 prior to starting a given measurement).

Experiments have shown that the synchronisation provided by the control system should preferably have a jitter (defined as a temporal synchronisation error of various control signals) preferably less than 500 μsec for neural activity measurements, more preferably less than 100 μsec, even more preferably less than 10 μsec for assessment of simultaneity in spike occurrences in different neural compartments. The small jitter allows for obtaining spatially and temporarily precisely synchronised measurement data, which is necessary to recognize e.g. that a certain measured signal is the result of certain stimulus. This low jitter can be achieved e.g. by connecting a dedicated control system 32 generating high speed signals with the components of the microscope system 10 via a common data bus with branches for each component. The length of the applied signal cables (e.g. data bus and branches) between the control system 32 and each controlled component may also influence synchronisation through the signal propagation speed, which is preferably taken into account in the design of the control system 32, as well as of the processing software.

The optical microscope system 10 according to the invention is suitable for simultaneous imaging—2D or 3D data collection—and optogenetic activation of neurons and neural processes in at least two (preferably three or more) brain regions. This opens the possibility of:

3D measurement of activity correlations and information spread from hundreds of neurons or neuronal processes in two, three or more functionally connected regions of interest 20, such as the visual system or the somatosensory system, optogenetic activation of neurons in two regions of interest 20 with different spatiotemporal patterns and measurement of signal integration in the neuronal network of the third region of interest 20, optogenetic activation in only one region of interest 20 with variable spatiotemporal patterns and the measurement of diverging activity in two other regions of interest 20, the ability to optogenetically silence cells in one brain region while imaging activity in other regions of interest 20, optogenetic activation of single cells in one region of interest 20, e.g. retina, and the measurement of how the signal propagates and is modified through the other regions of interest 20, such as the LGN and cortex.

The optical microscope system 10 according to the invention can be used to perform various measurements on the sensory systems of humans and animals. The Sensory systems typically comprise four functional parts 1) physical sensors, 2) relay stations 3) primer cortical area and 4) secondary cortical areas. In case of the visual system the detector is the retina, where the visual information is transformed to neuronal activity patterns, after which the information is transported by optical nerves to the lateral geniculate nucleus. The next step is performed in the visual cortex, then information is further processed in other brain areas such as the secondary visual cortex.

Each of the locations of the sensory pathway contains neuronal assemblies and are separated by several millimeters. The optical microscope system 10 according to the invention can provide for the first time simultaneous measurement (including data collection and/or photoactivation) in at least two regions of interest 20, in order to understand the whole process of vision. Ideally all four functional parts of the visual pathway must be simultaneously measured, but simultaneous measurement of only two regions in different combination may also map the whole vision processing system.

The same processing scheme applies also to other sensory systems. The same stages can be identified, although in inverted order, also in the motoric system. The optical microscope system 10 according to the present invention is capable to reveal processing details from different stages of the process by also providing the correlation between the activity of the distant centres. In this way the architecture of the new microscope system 10 can be extended to follow almost all sensing and motoric process controls and to study the operation of the nervous system as a whole.

In practice the optical microscope system 10 can be used to perform simultaneously or in a synchronised way various measurements, including photoactivation, in at least two spatially non-overlapping regions of interest. For example at least two spatially non-overlapping regions of interest can be selected where it is possible to perform scanning, photoactivation and measurement of one or more response signals in any number of the selected regions. It is also possible to perform multiple operations in the same region of interest (e.g. photoactivation and measurement of a response signal and/or scanning), but it is also possible to perform one type of operation in one region of interest, and another type of operation in another region of interest (e.g. photoactivation in a first region of interest and measuring a response signal and/or scanning in a second region of interest). In this way it is possible to examine the integration between various regions of interest (e.g. between various regions of the brain), depending on which region is activated and which region is selected to measure the effect of the activation.

It is also possible to perform the various measurements (including photoactivation) in a synchronised way, e.g. sequentially with a precisely defined time shift between the measurements (e.g. photoactivation followed by a measurement in the same or different region of interest).

Various modifications to the above disclosed embodiments will be apparent to a person skilled in the art without departing from the scope of protection determined by the attached claims.

The invention claimed is:

1. Optical microscope system for the simultaneous measurement of at least two spatially distinct regions of interest, comprising at least two scan heads and at least two distinct optical measuring heads that can be simultaneously focused on spatially non-overlapping arbitrary regions of interest, each optical measuring head being optically connectable with at least one scan head, the optical microscope system further comprising a control system connected to the at least one scan head and the optical measuring heads, the control system being configured to provide for synchronised control of the operation of the at least one scan head and the at least two optical measuring heads characterised by comprising an optical multiplexer having at least two output ports that are optically coupled to the at least two optical measuring heads and having at least two input ports that are optically coupled with the at least two scan heads and having selective filters within the optical multiplexer capable of creating optical beam paths between any one of the at least two input ports and any one of the at least two output ports.

2. Optical microscope system for the simultaneous measurement of at least two spatially distinct regions of interest, comprising at least two distinct optical measuring heads that can be simultaneously focused on spatially non-overlapping arbitrary regions of interest, each optical measuring head being optically connectable with at least one scan head, the optical microscope system further comprising a control system connected to the at least one scan head and the optical measuring heads, the control system being configured to provide for synchronised control of the operation of the at least one scan head and the at least two optical measuring heads, characterised by that the synchronisation provided by the control system has a jitter less than 500 μsec.

3. Optical microscope system according to claim 1, characterised by that the at least two distinct optical measuring heads can be simultaneously focused on spatially non-overlapping arbitrary regions of interest that are spaced apart from each other by at least 1 mm, preferably by at least 1 cm.

4. Optical microscope system according to claim 1, characterised by that the at least two distinct optical measuring heads have distinct optical axes.

5. Optical microscope system according to claim 1, characterised by comprising at least two scan heads, that are each optically connectable with at least one optical imaging means.

6. Optical microscope system according to claim 5, characterised by that each scan head is tuned for a different wavelength.

7. Optical microscope system according to claim 5, characterised by that each scan head is optically coupled to a light source, preferably laser source, or lamp capable of providing an optical beam having a wavelength that corresponds to wavelength to which the scan head is tuned.

8. Optical microscope system according to claim 5, characterised by that said at least two scan heads are tuned to same wavelength and are optically coupled with same light source.

9. Optical microscope system according to claim 1, characterised by that at least one optical measuring head of said at least two distinct optical measuring heads comprises a microscope objective.

10. Optical microscope system according to claim 1, characterised by that at least one optical measuring head of said at least two distinct optical measuring heads comprises a GRIN lens.

11. Optical microscope system according to claim 1, characterised by that at least one optical measuring head of said at least two distinct optical measuring heads comprises a lens designed as an optical adaptor for eye or other tissue stimulation and imaging.

12. Optical microscope system for the simultaneous measurement of at least two spatially distinct regions of interest, comprising at least two distinct optical measuring heads that can be simultaneously focused on spatially non-overlapping arbitrary regions of interest, each optical measuring head being optically connectable with at least one scan head, the optical microscope system further comprising a control system connected to the at least one scan head and the optical measuring heads, the control system being configured to provide for synchronised control of the operation of the at least one scan head and the at least two optical measuring heads, characterised by having three optical measuring heads: a first optical measuring head which comprises a microscope objective, a second optical measuring head which comprises a GRIN lens, and a third optical measuring head which comprises an optical adaptor for eye stimulation and imaging.

13. Optical microscope system according to claim 1, characterised by having at least two scan heads of which at least one scan head is suitable for performing 3-dimensional scanning.

14. Optical microscope system according to claim 1, characterised by having at least one scan head that is capable of photoactivation.

15. Optical microscope system for the simultaneous measurement of at least two spatially distinct regions of interest, comprising at least two scan heads and at least two distinct optical measuring heads that can be simultaneously focused on spatially non-overlapping arbitrary regions of interest, each optical measuring head being optically connectable with at least one scan head, the optical microscope system further comprising a control system connected to the at least one scan head and the optical measuring heads, the control system being configured to provide for synchronised control of the operation of the at least one scan head and the at least two optical measuring heads characterised by having at least two scan heads of which at least one scan head is suitable for performing 3-dimensional scanning.

* * * * *